US011243266B2

(12) United States Patent
Kim et al.

(10) Patent No.: US 11,243,266 B2
(45) Date of Patent: Feb. 8, 2022

(54) TRANSFORMER HYDROGEN GAS MONITORING SYSTEM, DEVICE, AND METHOD (71) Applicant: KOREA ELECTRIC POWER CORPORATION, Naju-si (KR)

(72) Inventors: Seok-Kon Kim, Daejeon (KR); Jeong-Yeol Han, Daejeon (KR); You-Jin Lee, Daejeon (KR); Tea-Kyun Kim, Daejeon (KR); Yong-Ho An, Daejeon (KR); Byung-Tae Jang, Daejeon (KR); Jong-Kee Choi, Daejeon (KR); Nam-Ho Lee, Daejeon (KR); Nam-Dae Kim, Daejeon (KR)

(73) Assignee: KOREA ELECTRIC POWER CORPORATION, Naju-si (KR)

( * ) Notice: Subject to any disclaimer, the term of this patent is extended or adjusted under 35 U.S.C. 154(b) by 237 days.

(21) Appl. No.: 16/491,382

(22) PCT Filed: Aug. 18, 2017

(86) PCT No.: PCT/KR2017/008994
§ 371 (c)(1),
(2) Date: Sep. 5, 2019

(87) PCT Pub. No.: WO2018/164331
PCT Pub. Date: Sep. 13, 2018

(65) Prior Publication Data
US 2020/0033280 A1   Jan. 30, 2020

(30) Foreign Application Priority Data
Mar. 10, 2017  (KR) .................. 10-2017-0030662

(51) Int. Cl.
*G01N 27/04*   (2006.01)
*G01N 33/28*   (2006.01)
(Continued)

(52) U.S. Cl.
CPC ............. *G01R 31/62* (2020.01); *G01N 27/04* (2013.01); *G01N 33/005* (2013.01);
(Continued)

(58) Field of Classification Search
CPC ........ G01R 31/62; G01R 27/02; G01R 31/12; G01R 31/1281; G01N 27/04;
(Continued)

(56) References Cited

U.S. PATENT DOCUMENTS

| 6,450,007 B1 * | 9/2002 | O'Connor | G01N 27/12 338/34 |
| 2004/0261500 A1 * | 12/2004 | Ng | B82Y 15/00 73/31.05 |
| 2005/0155858 A1 * | 7/2005 | Monty | G01N 33/005 204/424 |
| 2008/0154434 A1 * | 6/2008 | Galloway | G01N 33/005 700/271 |

(Continued)

FOREIGN PATENT DOCUMENTS

| KR | 20-0284076 Y1 | 7/2002 |
| KR | 10-2007-0046575 A | 5/2007 |

(Continued)

*Primary Examiner* — Christopher P McAndrew
*Assistant Examiner* — Zannatul Ferdous
(74) *Attorney, Agent, or Firm* — Foundation Law Group, LLP (57) ABSTRACT A transformer hydrogen gas monitoring system according to an embodiment of the present invention may comprise: a sensor module, which is disposed to allow at least a part thereof to meet hydrogen gas in a transformer and measures a resistance value of a member having a variable resistance value according to a hydrogen concentration in the transformer; and a multi-task module for receiving a sensing result of the sensor module, generating hydrogen concentration information corresponding to resistance value information included in the sensing result, and remotely transmitting information corresponding to the generated hydrogen concentration information.

19 Claims, 4 Drawing Sheets (51) Int. Cl.
  *G01N 33/00* (2006.01)
  *G01R 27/02* (2006.01)
  *H01F 27/40* (2006.01)
  *G01R 31/12* (2020.01)
  *H01F 27/14* (2006.01)
  *G01R 31/62* (2020.01)
  *G08C 17/02* (2006.01)

(52) U.S. Cl.
  CPC ......... *G01N 33/2841* (2013.01); *G01R 27/02* (2013.01); *G01R 31/12* (2013.01); *G08C 17/02* (2013.01); *H01F 27/14* (2013.01); *H01F 27/402* (2013.01)

(58) Field of Classification Search
  CPC ............. G01N 33/005; G01N 33/2841; G01N 27/127; G08C 17/02; H01F 27/14; H01F 27/402; H01F 2027/404
  See application file for complete search history.

(56) References Cited

U.S. PATENT DOCUMENTS

| | | | |
|---|---|---|---|
| 2009/0281673 A1* | 11/2009 | Taft | G01R 22/063 |
| | | | 700/286 |
| 2012/0247187 A1 | 10/2012 | Herz | |
| 2013/0024131 A1 | 1/2013 | Lamontagne | |
| 2017/0133836 A1* | 5/2017 | Potnis | H02H 3/066 |
| 2018/0044819 A1* | 2/2018 | Inoue | D02G 3/38 |

FOREIGN PATENT DOCUMENTS

| KR | 10-2012-0008240 A | 1/2012 |
|---|---|---|
| KR | 10-1221881 B1 | 1/2013 |
| KR | 10-2013-0061524 A | 6/2013 |
| KR | 10-2014-0055652 A | 5/2014 |
| KR | 10-2015-0107364 A | 9/2015 |
| KR | 10-1579484 B1 | 12/2015 |
| KR | 10-1761838 B1 | 7/2017 |

* cited by examiner

TRANSFORMER HYDROGEN GAS MONITORING SYSTEM, DEVICE, AND METHOD

CROSS REFERENCE TO RELATED PATENT APPLICATION(S)

This application claims the benefit under 35 U.S.C. Section 371, of PCT International Application No. PCT/KR2017/008994, filed on Aug. 18, 2018, which claimed priority to Korean Patent Application No. KR 10-2017-0030662, filed on Mar. 10, 2017, the disclosures of which are hereby incorporated by the references.

TECHNICAL FIELD

The present disclosure relates to transformer hydrogen gas monitoring system, device and method.

BACKGROUND ART

As an aging failure phenomenon in transformers installed in the field has increased recently, the necessity of establishing a preventive diagnosis system in preparation for aging failure is increasing. A transformer preventive diagnosis may be performed through gas chromatograph (GC) in the transformer.

Conventional transformer preventive diagnosis was performed by a method of extracting gas from the transformer through a filter (membrane) and analyzing the extracted gas. Such a method is expensive for maintenance, such as filter replacement, which leads to longer transformer preventive diagnosis cycle. The aging failure of the transformer may frequently occur during the transformer preventive diagnosis cycle.

DISCLOSURE

Technical Problem

An aspect of the present disclosure is to provide transformer hydrogen gas monitoring system, device and method for providing an environment that may simplify an analysis of the hydrogen gas in a transformer so as to reduce a transformer preventive diagnosis cycle.

Technical Solution

According to an aspect of the present disclosure, a transformer hydrogen gas monitoring system includes a sensor module measuring a resistance value of a member having at least a portion disposed to meet the hydrogen gas in the transformer and having a variable resistance value according to a hydrogen concentration in the transformer; and a multi-task module receiving a detection result of the sensor module, generating hydrogen concentration information corresponding to resistance value information included in the detection result, and remotely transmitting information corresponding to the generated hydrogen concentration information.

The member may include carbon nanotubes.

The sensor module may further include a temperature control unit that changes a temperature of the member, and the multi-task module may control an operation of the temperature control unit so that the temperature of the member is outside of a predetermined temperature range after receiving a first detection result during a first measurement period of the sensor module, control the operation of the temperature control unit so that the temperature of the member falls within the predetermined temperature range after the temperature of the member is outside of the predetermined temperature range, and receive a second detection result during a second measurement period of the sensor module when the temperature of the member falls within the predetermined temperature range.

The sensor module may further include a position control unit that changes a position of the member, and the multi-task module may control an operation of the position control unit so that the member is not located in the transformer after receiving a first detection result during a first measurement period of the sensor module, control the operation of the position control unit so that at least a portion of the member is located in the transformer, and receive a second detection result during a second measurement period of the sensor module when at least a portion of the member is located in the transformer.

The member may be disposed in an oil drain valve so that insulating oil included in the transformer does not pass through the oil drain valve.

The sensor module may further include a temperature sensor measuring a temperature in the transformer; and a cable electrically connecting between the sensor module and the multi-task module, and the multi-task module may generate the hydrogen concentration information by applying the temperature in the transformer, the resistance value of the member, and a resistance value of the cable to a predetermined equation.

At least one of a length, a thickness and resistivity of the cable may be designed so that the resistance value of the cable is lower than the resistance value of the member.

The multi-task module may generate state information of the transformer corresponding to the generated hydrogen concentration information and remotely transmit the generated state information, and the state information may include at least two of a partial discharge, an arc, and an overheating.

The system may further include a HMI receiving information corresponding to the hydrogen concentration information from the multi-task module, wherein the HMI may transmit a control signal to the multi-task module, and the multi-task module may control an on-off operation of the transformer based on the control signal.

According to another aspect of the present disclosure, a transformer hydrogen gas monitoring device includes a sensing unit receiving resistance value information of a member having at least a portion disposed to meet the hydrogen gas in the transformer and having a variable resistance value according to a hydrogen concentration in the transformer; a calculation unit calculating hydrogen concentration information in the transformer based on the resistance value information of the member; and a communications unit generating a communications signal including the hydrogen concentration information in the transformer and remotely transmitting the communications signal.

The device may further include a control unit repeatedly controlling a temperature or a position of the member every predetermined cycle.

The sensing unit may receive temperature information of the member, and the device may further include a compensating unit compensating for the resistance value information by applying the temperature information and the resistance value information to a predetermined equation.

The sensing unit may be electrically connected to the member through a cable, and the compensating unit may compensate for the resistance value information by applying a resistance value of the cable to the predetermined equation.

According to another aspect of the present disclosure, a transformer hydrogen gas monitoring method includes detecting a resistance value of a member having at least a portion disposed to meet the hydrogen gas in the transformer and having a variable resistance value according to a hydrogen concentration in the transformer; calculating hydrogen concentration information in the transformer based on resistance value information of the member; and generating a communications signal including the hydrogen concentration information in the transformer and remotely transmitting the communications signal.

Advantageous Effects

As set forth above, according to an exemplary embodiment in the present disclosure, since the transformer hydrogen gas monitoring system, device and method according to an exemplary embodiment in the present disclosure may perform the gas analysis without extracting the gas in the transformer, the cost of the preventive diagnosis process on a large number of transformers may be reduced, and the preventive diagnosis process may be simplified.

The simplification of the preventive diagnosis process may lead to shortening of the transformer preventive diagnosis cycle, and may be the basis for establishing the environment in which the manager may monitor the gas in the transformer in real time.

Therefore, the transformer hydrogen gas monitoring system, device and method according to an exemplary embodiment in the present disclosure may collectively collect the hydrogen concentration information from the large number of transformers, and may support accurate transformer fault sign diagnosis and management through analysis of the collected hydrogen concentration information.

BEST MODE FOR INVENTION

Exemplary embodiments of the present invention will be described in detail with reference to the accompanying drawings. It should be appreciated that various exemplary embodiments of the present invention are different from each other, but do not have to be exclusive. For example, specific shapes, structures, and characteristics described in the present specification may be implemented in another exemplary embodiment without departing from the spirit and the scope of the present invention in connection with an exemplary embodiment. In addition, it should be understood that a position or an arrangement of individual components in each disclosed exemplary embodiment may be changed without departing from the spirit and the scope of the present invention. Therefore, a detailed description described below should not be construed as being restrictive. In addition, the scope of the present invention is defined only by the accompanying claims and their equivalents if appropriate. Similar reference numerals will be used to describe the same or similar functions throughout the accompanying drawings.

Hereinafter, embodiments of the present invention will be described in detail with reference to the accompanying drawings so that those skilled in the art may easily practice the present invention.

Figure 1:
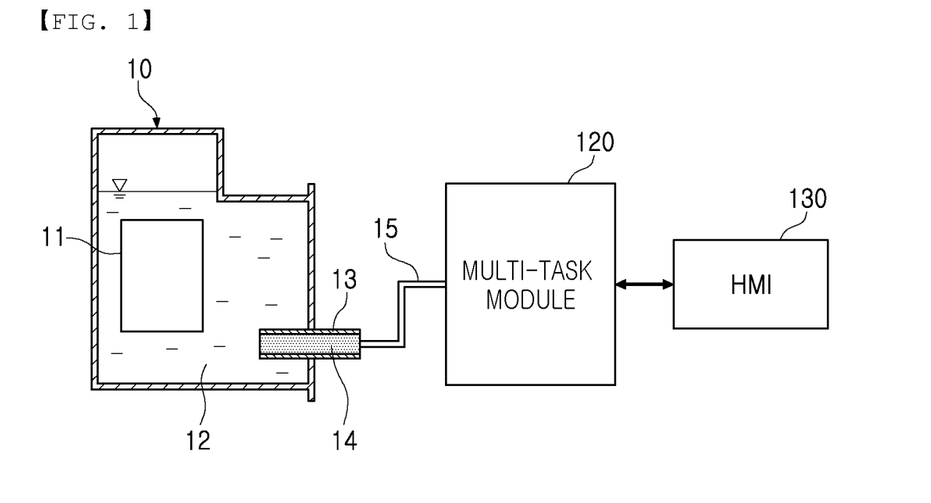
FIG. 1 is a conceptual diagram illustrating a transformer hydrogen gas monitoring system according to an exemplary embodiment in the present disclosure.

FIG. 1 is a conceptual diagram illustrating a transformer hydrogen gas monitoring system according to an exemplary embodiment in the present disclosure.

Referring to FIG. 1, a system for monitoring gas according to an exemplary embodiment in the present disclosure may include at least some of a sensor module including a member 14, a multi-task module 120, and a HMI 130, and may monitor gas in a transformer 10.

The member 14 may have at least a portion thereof disposed in the transformer 10 and may have a variable resistance value according to a hydrogen concentration.

For example, the member 14 may be implemented with carbon nanotubes (CNT), and may be disposed in an oil drain valve 13 so that one end thereof is located in the transformer 10 and the other end thereof is located outside the transformer 10. In addition, the member 14 may include a structure such as a partition wall to prevent insulating oil 12 from passing through the oil drain valve 13.

The sensor module may be electrically connected to the member 14 to measure the resistance value of the member 14. For example, the sensor module may include a gas sensor electrically connected to the other end of the member 14 to apply a sensing voltage and measure a sensing current according to the sensing voltage.

Accordingly, since the system for monitoring gas according to an exemplary embodiment in the present disclosure may perform a gas analysis without extracting the gas in the transformer, the cost of a preventive diagnosis process on a large number of transformers may be reduced, and the preventive diagnosis process may be simplified. The simplification of the preventive diagnosis process may lead to shortening of a transformer preventive diagnosis cycle, and may be the basis for establishing an environment in which the gas in the transformer may be monitored in real time.

In addition, the sensor module may further include a cable 15 that electrically connects between the member 14 and the multi-task module 120. Therefore, the gas sensor may be disposed in the multi-task module 120 to apply the sensing voltage through the cable 15 and measure the sensing current.

Since a measurement accuracy when the sensor module measures the resistance value of the member 14 through the cable 15 is higher as a resistance value of the cable 15 is smaller, the cable 15 may be short or thick to have a small resistance value. For example, at least one of the length, thickness and resistivity of the cable 15 may be designed such that the resistance value of the cable 15 is smaller than the resistance value of the member 14. Accordingly, the multi-task module 120 may be disposed to be adjacent to the transformer 10.

The multi-task module 120 may receive a detection result of the sensor module, generate hydrogen concentration information corresponding to resistance value information included in the detection result, and remotely transmit information corresponding to the generated hydrogen concentration information. The information corresponding to the hydrogen concentration information may include at least one of hydrogen concentration information, resistance value information, and state information of the transformer. For example, the multi-task module 120 may be design in the same manner as the transformer hydrogen gas monitoring device illustrated in FIG. 2.

The HMI 130 may receive the information corresponding to the hydrogen concentration information from the multi-task module 120. For example, the HMI 130 may provide an environment in which a manager may monitor the transformer in real time without restriction of time and place based on the Internet of Things (IoT).

The HMI 130 may provide the hydrogen concentration information in real time to the manager in the field, and may accumulate and store the hydrogen concentration information for a long time to perform an in-deep analysis for the accumulated hydrogen concentration information. In addition, the HMI 130 may transmit a control signal to the multi-task module 120 to control an on-off operation of the transformer 10 based on the hydrogen concentration information. Thereafter, the multi-task module 120 may control the on-off operation of the transformer 10 based on the control signal. Accordingly, the system for monitoring gas according to an exemplary embodiment in the present disclosure may collectively monitor the gas of a large number of transformers and take quick and accurate action on transformers with fault signs.

Figure 2:
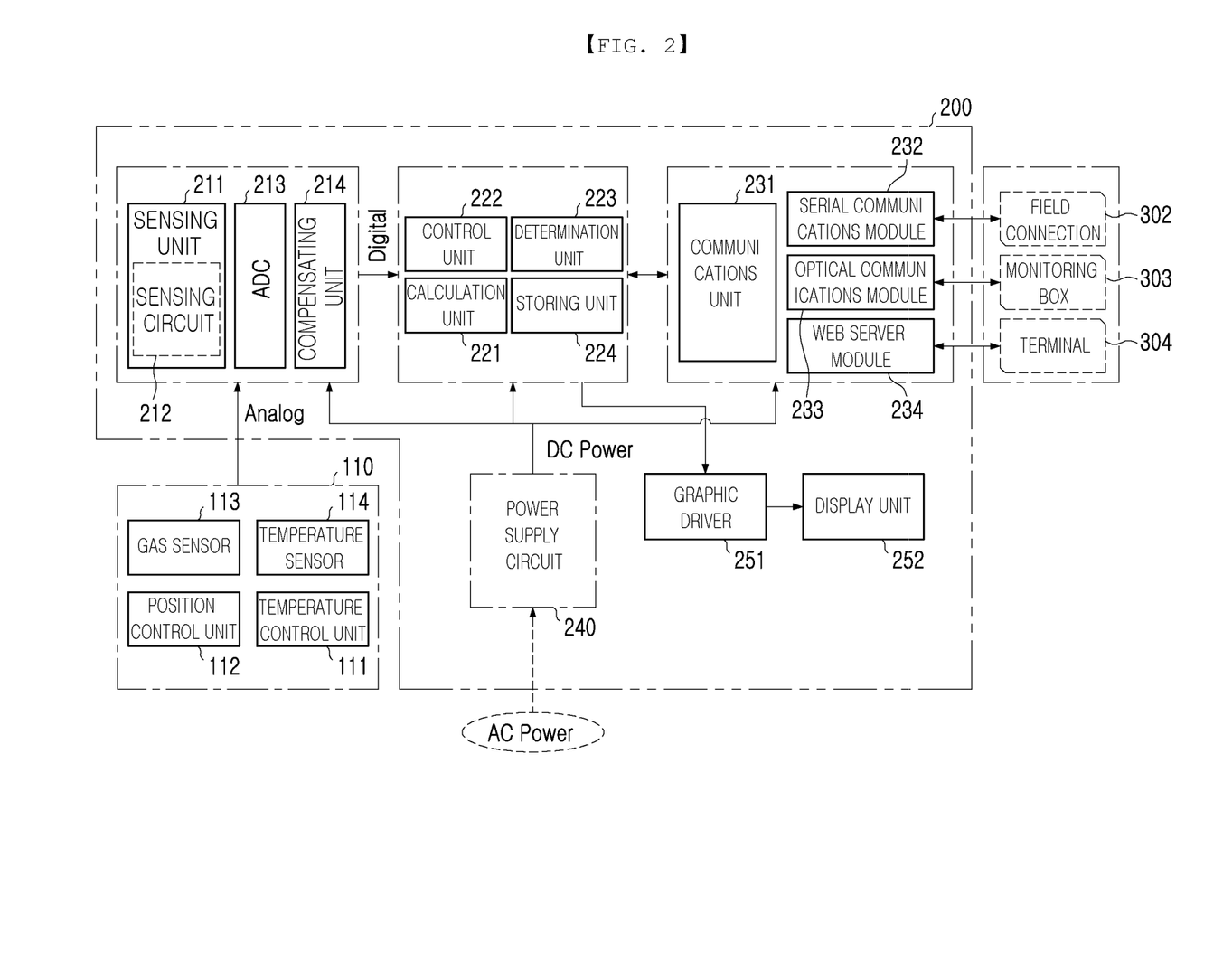
FIG. 2 is a diagram illustrating the transformer hydrogen gas monitoring system and device according to an exemplary embodiment in the present disclosure.

FIG. 2 is a diagram illustrating the transformer hydrogen gas monitoring system and device according to an exemplary embodiment in the present disclosure.

Referring to FIG. 2, the sensor module 110 may include at least some of a temperature control unit 111, a position control unit 112, a gas sensor 113, and a temperature sensor 114.

The temperature control unit 111 may change a temperature of the member 14. Since the hydrogen concentration in the transformer may fluctuate over time, the temperature control unit 111 may control the temperature of the member 14 such that hydrogen smeared with a surface of the member 14 or permeated into the member 14 is removed whenever being measured. Accordingly, hydrogen concentration measurement accuracy may be improved.

For example, the temperature control unit 111 may quickly remove hydrogen in the member 14 by heating a portion of the member 14 located outside the transformer to about 50 degrees, and may leave the member 14 or cool the member 14 after heating.

For example, the temperature control unit 111 may receive a temperature control signal from a control unit 222 of the transformer hydrogen gas monitoring device 200 and raise or lower the temperature of the member 14 according to the temperature control signal.

That is, the temperature control unit 111 may heat the member 14 so that the temperature of the member 14 is outside of a predetermined temperature range and cool the member 14 so that the temperature of the member 14 falls within the predetermined temperature range, during a temperature control period between a first measurement period and a second measurement period.

Here, the first measurement period and the second measurement period may be set based on a time point at which the gas sensor 113 transmits the measurement result to a sensing unit 211. Meanwhile, the predetermined temperature range may be room temperature of about 25 degrees, but is not limited thereto.

The position control unit 112 may change a position of the member 14. Since the hydrogen concentration in the transformer may fluctuate over time, the position control unit 112 may move the member 14 outside the transformer or insert the member 14 into the transformer such that hydrogen smeared with a surface of the member 14 or permeated into the member 14 is removed whenever being measured. Accordingly, hydrogen concentration measurement accuracy may be improved.

For example, the position control unit 112 may pick up a portion of the member 14 located outside the transformer to move the member 14 outside the transformer, and may block the oil drain valve to prevent the insulating oil in the transformer from passing through the oil drain valve after the member 14 moves. Thereafter, the position control unit 112 may insert the member 14 into the oil drain valve while opening the oil drain valve.

For example, the position control unit 112 may receive a position control signal from the control unit 222 of the transformer hydrogen gas monitoring device 200 and control the movement of the member 14 according to the position control signal.

That is, the position control unit 112 may move the member 14 so that the member 14 is not located in the transformer and move the member 14 so that the member 14 is located in the transformer, during a position control period between the first measurement period and the second measurement period.

Meanwhile, the temperature control of the temperature control unit 111 and the position control of the position control unit 112 may be performed together. Since the resistance value of the member 14 immediately after the member 14 is cooled or immediately after the member 14 is inserted into the transformer may not accurately reflect an actual hydrogen concentration of the transformer 10, the length of the first measurement period and the second measurement period may be set to about 10 hours for hydrogen concentration measurement accuracy, but is not limited thereto.

The gas sensor 113 may secure hydrogen concentration information in the transformer by measuring the resistance value of the member 14. For example, the gas sensor 113 may be designed in the same manner as the sensor module described above with reference to FIG. 1.

The temperature sensor 114 can measure a temperature in the transformer. A relationship between the resistance value of the member 14 and the hydrogen concentration in the transformer may be influenced by the temperature in the transformer. Therefore, the temperature sensor 114 may transmit information on the measured temperature to the sensing unit 211 or a compensating unit 214, thereby allowing a calculation unit 221 to reflect the temperature information measured in the process of generating the hydrogen concentration information. Accordingly, hydrogen concentration measurement accuracy may be improved.

Referring to FIG. 2, the transformer hydrogen gas monitoring device 200 according to an exemplary embodiment in the present disclosure may include at least some of the sensing unit 211, a sensing circuit 212, an ADC 213, the compensating unit 214, the calculation unit 221, the control unit 222, a determination unit 223, a storing unit 224, a communications unit 231, a serial communications module 232, an optical communications module 233, a web server module 234, a power supply circuit 240, a graphic driver 251, and a display unit 252, and may be integrally designed to receive the detection result from the sensor module 110 and perform multiple functions.

The sensing unit 211 may receive resistance value information of the member 14 from the gas sensor 113.

For example, the sensing unit 211 may include the sensing circuit 212 that applies a sensing voltage to the cable 15, measures a sensing current according to the sensing voltage, and amplifies or filters the sensing current in order to receive the resistance value information of the member 14. Accordingly, the transformer hydrogen gas monitoring device 200 may precisely measure the hydrogen concentration even when a resistance value change ratio of the member 14 according to the change in the hydrogen concentration in the transformer is small.

The ADC 213 may convert an output signal of the sensing circuit 212 into a digital value.

The compensating unit 214 may compensate for the resistance value of the resistance value information by applying the temperature information generated by the temperature sensor 114 and the resistance value information generated by the gas sensor 113 to a predetermined equation. For example, the predetermined equation may include Equation 1 below. Here, R is a compensated resistance value, T is the temperature measured by the temperature sensor 114, α is a temperature coefficient of the member, $R_r$ is a resistance value of the member when the temperature is T degrees, and $R_a$ is a resistance value when the temperature is 0 degree. The temperature in the transformer varies by 3 to 9 degrees during the measurement period, but is not limited thereto.

$$R=R_r-(R_a+\alpha T) \quad \text{[Equation 1]}$$

The calculation unit 221 may calculate the hydrogen concentration information in the transformer based on the resistance value information of the member 14.

For example, the calculation unit 221 may calculate the hydrogen concentration information through Equation 2 below. Here, C is the hydrogen concentration, and β is hydrogen concentration sensitivity of the member. The unit of the hydrogen concentration is ppm, and the hydrogen concentration may be calculated around 1000 ppm, but is not limited thereto.

$$C = \frac{R_r - (R_a + \alpha T)}{\beta} \quad \text{[Equation 2]}$$

In addition, the calculation unit 221 may reflect the resistance value of the cable 15 to the hydrogen concentration calculation by applying Equation 3 below to Equation 2. Here, $R_a$ is resistivity of the cable 15, and $R_i$ is the resistance value of the member.

$$R_r=R_s+R_i \quad \text{[Equation 3]}$$

Accordingly, hydrogen concentration measurement accuracy may be improved.

The control unit 222 may generate a temperature control signal or a position control signal to repeatedly control the temperature or the position of the member 14 at predetermined intervals.

The determination unit 223 may generate state information of the transformer corresponding to the hydrogen concentration information calculated by the calculation unit 221. Here, the state information may include at least two of a partial discharge, an arc, and overheating. For example, a gas generation ratio for each of the fault phenomena of the transformer may be as illustrated Table 1 below.

TABLE 1

| classification | Partial Discharge (Corona PD) | Arc | Overheating (Thermal fault) |
|---|---|---|---|
| H2 | 88% | 39% | 16% |
| C2H2 | 0.2% | 35% | — |
| C2H4 | 0.1% | 6% | 41% |

Referring to Table 1, a hydrogen ratio generated by the arc generation may be lower than the hydrogen ratio generated by a partial discharge occurrence, and may be higher than the hydrogen ratio generated by an overheating occurrence.

For example, the determination unit 223 may set a first range of a high hydrogen concentration range, a second range of an intermediate hydrogen concentration range, and a third range of a low hydrogen concentration range, determine the state information of the transformer as the partial discharge when the hydrogen concentration information calculated by the calculation unit 221 corresponds to the first range, determine the state information of the transformer as the arc when the hydrogen concentration information calculated by the calculation unit 221 corresponds to the second range, and determine the state information of the transformer as the overheating when the hydrogen concentration information calculated by the calculation unit 221 corresponds to the third range.

The storing unit 224 may store the equations used for calculating the hydrogen concentration by the calculation unit 221, the information used for generating the control signal by the control unit 222, and the hydrogen concentration range used for determining the state information of the transformer by the determination unit 223. In addition, the storing unit 224 may include a shared memory to support queuing of the communications unit 231.

The communications unit 231 may generate a communications signal including the hydrogen concentration information in the transformer and/or the state information of the transformer, and remotely transmit the communications signal to a field connection 302, a monitoring box 303, or a terminal 304.

The serial communications module 232 may provide a serial communications environment of the communications unit 231.

The optical communications module 233 may provide an optical communications environment of the communications unit 231.

The web server module 234 may provide an online access environment of the communications unit 231.

The power supply circuit 240 may receive alternating current (AC) power, convert the AC power into direct current (DC) power, and supply the DC power to the sensing unit 211, the compensating unit 214, the calculation unit 221, and the communications unit 231. For example, the power supply circuit 240 may include a switched-mode power supply (SMPS) and a surge protection circuit (SPC), and include a battery and a DC-DC converter to use stored power instead of receiving the AC power.

The graphic driver 251 may perform a graphic processing operation to generate a graph or chart including the hydrogen concentration information and/or the state information of the transformer calculated by the calculation unit 221.

The display unit 252 may display the graph or chart generated by the graphic driver 251. The manager may view a display image of the display unit 52, quickly detect the hydrogen concentration information of the transformer and/or the state information of the transformer, and take an action on the transformer.

Figure 3:
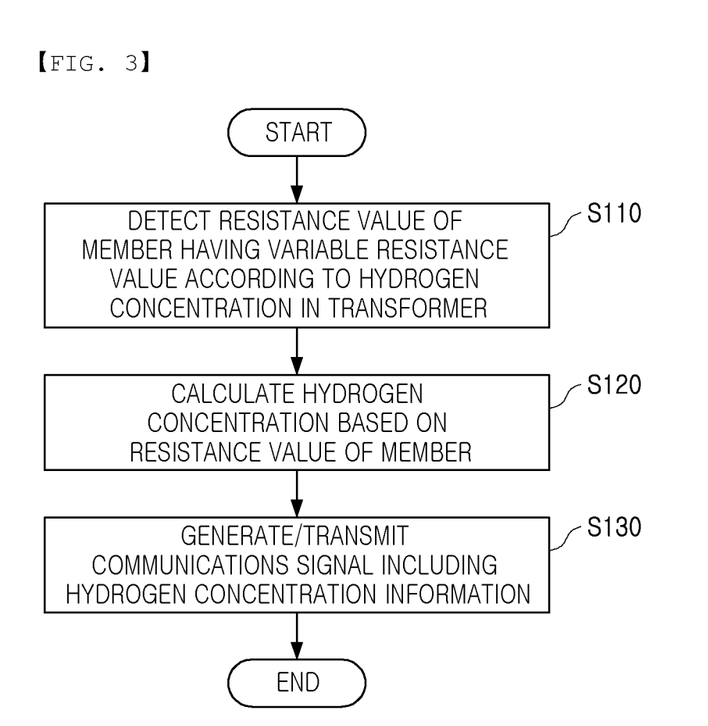
FIG. 3 is a flowchart illustrating a transformer hydrogen gas monitoring method according to an exemplary embodiment in the present disclosure.

FIG. 3 is a flowchart illustrating a transformer hydrogen gas monitoring method according to an exemplary embodiment in the present disclosure.

Referring to FIG. 3, a transformer hydrogen gas monitoring method according to an exemplary embodiment in the present disclosure may include an operation (S110) of detecting a resistance value of a member, an operation (S120) of calculating a hydrogen concentration information in the transformer based on the detected resistance value, and an operation (S130) of generating a communications signal including the hydrogen concentration information in the transformer and remotely transmitting the communications signal.

For example, the transformer hydrogen gas monitoring method may be performed by the transformer hydrogen gas monitoring system or the transformer hydrogen gas monitoring device illustrated in FIGS. 1 and 2.

Figure 4:
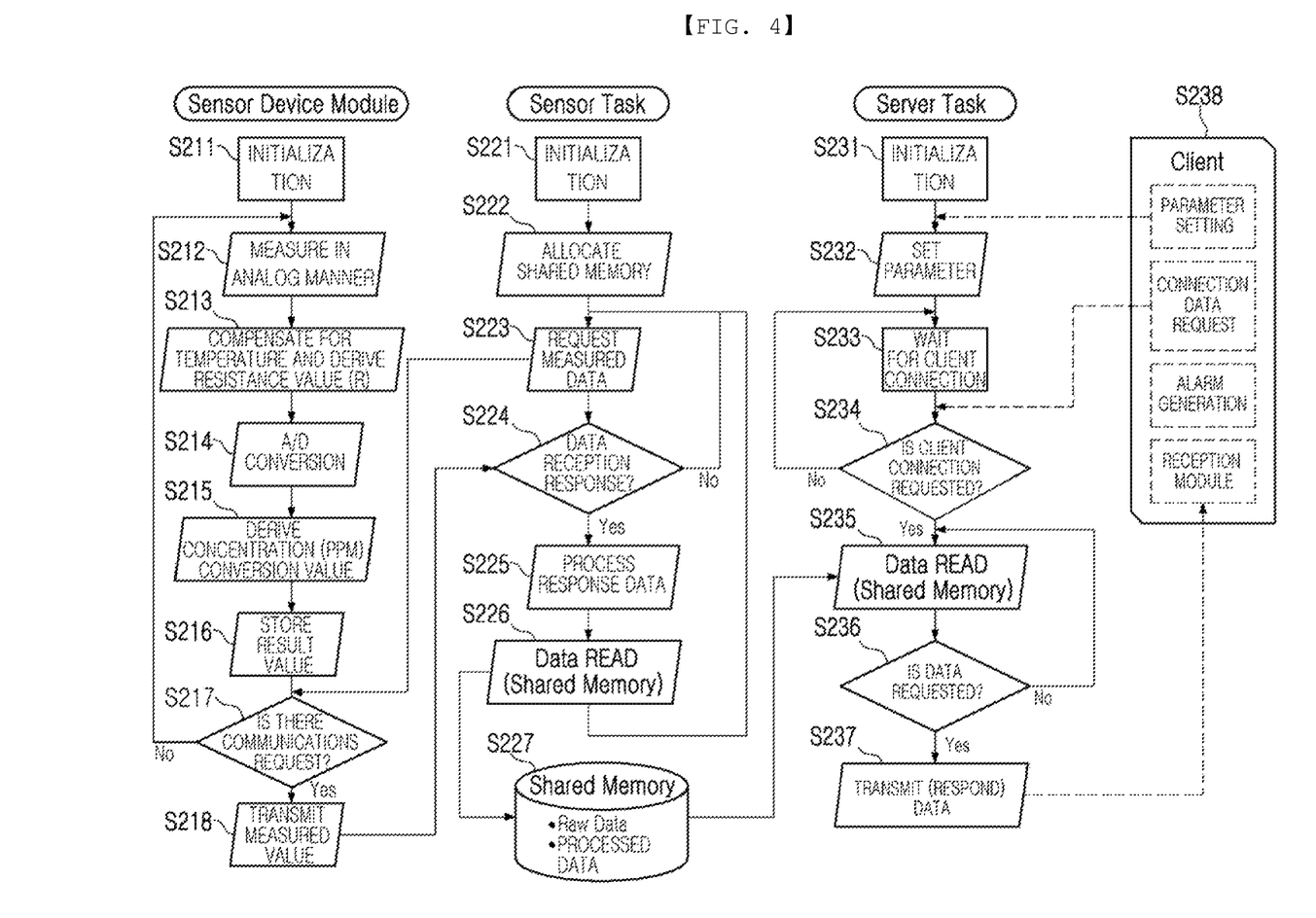
FIG. 4 is a flowchart specifically illustrating the transformer hydrogen gas monitoring method according to an exemplary embodiment in the present disclosure.

FIG. 4 is a flowchart specifically illustrating the transformer hydrogen gas monitoring method according to an exemplary embodiment in the present disclosure.

Referring to FIG. 4, the sensor module may initialize a measurement environment (S211), measure the resistance value of the member in an analog manner (S212), derive a compensated resistance value by performing temperature compensation on the measured resistance value (S213), convert an analog signal having the derived resistance value information into a digital value (S214), derive a concentration conversion value in order to generate hydrogen concentration information based on the resistance value information (S215), store a hydrogen concentration result value (S216), checks whether there is a communications request from the multi-task module (S217), and transmit a measured value when there is the communications request (S218).

Referring to FIG. 4, the multi-task module (sensor task) may initialize an operation environment (S221), allocate a shared memory (S222), request measured data to the sensor module (S223), check a measurement value reception response from the sensor module (S224), process response data when there is the reception response (S225), write data (S226), and store the written data in the shared memory (S227).

Referring to FIG. 4, the server (server task) may initialize an operation environment (S231), receive a parameter from a client to set the parameter (S232), wait for a client connection (S233), check whether the client connection is requested (S234), read and write data from the shared memory (S227) when there is the connection request (S235), check whether the client requests data (S236), and transmit the data to the client when there is the data request.

Referring to FIG. 4, an operation (S238) of the client may include a parameter setting, a connection data request, a data reception, and an alarm generation according to the received data. The client may be the field connection 302, the monitoring box 303, or the terminal 304 illustrated in FIG. 2. That is, the server may perform a relay operation between the field connection 302, the monitoring box 303, or the terminal 304 and the multi-task module.

Meanwhile, the transformer hydrogen gas monitoring method according to an exemplary embodiment in the present disclosure may be performed by a computing environment including a processor, a memory, a storage, an input device, an output device, and a communications connection. For example, the input device may correspond to the sensing unit illustrated in FIG. 2, the processor may correspond to the calculation unit, the control unit, or the determination unit illustrated in FIG. 2, the memory may correspond to the storing unit illustrated in FIG. 2, and storage may support an update operation of the memory, and the output device may correspond to the display unit illustrated in FIG. 2.

In addition, the term '~ unit' used in the present exemplary embodiment refers to software or a hardware component such as a field-programmable gate array (FPGA) or an ASIC, and '~ unit' performs certain roles. However, '~ unit' is not meant to be limited to software or hardware. '~ unit' may be configured to be in an addressable storage medium or may also be configured to reproduce one or more processors. Therefore, as an example, '~ unit' includes components such as software components, object-oriented software components, class components, and task components, processes, functions, attributes, procedures, subroutines, segments of program code, drivers, firmware, microcode, circuitry, data, database, data structures, tables, arrays, and variables. The functions provided within the components and the '~ units' may be combined into a smaller number of components and '~ units', or further divided into additional components and '~ units'. As well, the components and '~ units' may also be implemented to reproduce one or more CPUs in a device or a system.

While exemplary embodiments have been shown and described above, it will be apparent to those skilled in the art that modifications and variations could be made without departing from the scope of the present invention as defined by the appended claims.

The invention claimed is:

1. A transformer hydrogen gas monitoring system, the system comprising:
   a sensor module measuring a resistance value of a member having at least a portion disposed to meet the hydrogen gas in the transformer and having a variable resistance value according to a hydrogen concentration in the transformer; and
   a computing environment configured to receive a detection result of the sensor module, generate hydrogen concentration information corresponding to resistance value information included in the detection result, and remotely transmit information corresponding to the generated hydrogen concentration information,
   wherein the sensor module further includes:
   a temperature sensor measuring a temperature in the transformer; and
   a cable electrically connecting between the sensor module and the computing environment, and
   the computing environment configured to generate the hydrogen concentration information by applying the temperature in the transformer, the resistance value of the member, and a resistance value of the cable to a predetermined equation.

2. The system of claim 1, wherein the member includes carbon nanotubes.

3. The system of claim 1, wherein the sensor module further includes a temperature controller configured to change a temperature of the member, and
   the computing environment is configured to control an operation of the temperature controller so that the temperature of the member is outside of a predetermined temperature range after receiving a first detection result during a first measurement period of the sensor module, control the operation of the temperature controller so that the temperature of the member falls within the predetermined temperature range after the temperature of the member is outside of the predetermined temperature range, and receive a second detection result during a second measurement period of the sensor module when the temperature of the member falls within the predetermined temperature range.

4. The system of claim 1, wherein the sensor module further includes a position controller that is configured to change a position of the member, and the computing environment is configured to control an operation of the position controller so that the member is not located in the transformer after receiving a first detection result during a first measurement period of the sensor module, control the operation of the position controller so that at least a portion of the member is located in the transformer, and receive a second detection result during a second measurement period of the sensor module when at least a portion of the member is located in the transformer.

5. The system of claim 1, wherein the member is disposed in an oil drain valve so that insulating oil included in the transformer does not pass through the oil drain valve.

6. The system of claim 1, wherein the computing environment is configured to calculate the hydrogen concentration by using the following equation:

$$C = \frac{R_r - (R_a + \alpha T)}{\beta}$$

$$R_r = R_s + R_i$$

as the predetermined equation, and in the equation, C is the hydrogen concentration, T is the temperature measured by the temperature sensor, $\alpha$ is a temperature coefficient of the member, $\beta$ is a hydrogen concentration sensitivity of the member, $R_r$ is a resistance value when the temperature measured by the temperature sensor is T degrees, $R_a$ is a resistance value when the temperature measured by the temperature sensor is 0 degrees, $R_s$ is the resistance value of the cable, and $R_i$ is the resistance value of the member.

7. The system of claim 1, wherein at least one of a length, a thickness and resistivity of the cable is designed so that the resistance value of the cable is lower than the resistance value of the member.

8. The system of claim 1, wherein the computing environment is configured to generate state information of the transformer corresponding to the generated hydrogen concentration information and remotely transmits the generated state information, and the state information includes at least two of a partial discharge, an arc, and an overheating.

9. The system of claim 1, further comprising a human-machine interface (HMI) receiving information corresponding to the hydrogen concentration information from the computing environment, wherein the HMI transmits a control signal to the computing environment, and the computing environment is configured to control an on-off operation of the transformer based on the control signal.

10. A transformer hydrogen gas monitoring system, the system comprising:

a sensor module measuring a resistance value of a member having at least a portion disposed to meet the hydrogen gas in the transformer and having a variable resistance value according to a hydrogen concentration in the transformer; and a computing environment configured to receive a detection result of the sensor module, generate hydrogen concentration information corresponding to resistance value information included in the detection result, and remotely transmit information corresponding to the generated hydrogen concentration information, wherein the sensor module further includes a temperature controller configured to change a temperature of the member, and the computing environment is configured to control an operation of the temperature controller so that the temperature of the member is outside of a predetermined temperature range after receiving a first detection result during a first measurement period of the sensor module, control the operation of the temperature controller so that the temperature of the member falls within the predetermined temperature range after the temperature of the member is outside of the predetermined temperature range, and receive a second detection result during a second measurement period of the sensor module when the temperature of the member falls within the predetermined temperature range.

11. The system of claim 10, wherein the member includes carbon nanotubes.

12. The system of claim 10, wherein the member is disposed in an oil drain valve so that insulating oil included in the transformer does not pass through the oil drain valve.

13. The system of claim 10, wherein the computing environment is configured to generate state information of the transformer corresponding to the generated hydrogen concentration information and remotely transmits the generated state information, and the state information includes at least two of a partial discharge, an arc, and an overheating.

14. The system of claim 10, further comprising a human-machine interface (HMI) receiving information corresponding to the hydrogen concentration information from the computing environment, wherein the HMI transmits a control signal to the computing environment, and the computing environment is configured to control an on-off operation of the transformer based on the control signal.

15. A transformer hydrogen gas monitoring system, the system comprising:

a sensor module measuring a resistance value of a member having at least a portion disposed to meet the hydrogen gas in the transformer and having a variable resistance value according to a hydrogen concentration in the transformer; and a computing environment configured to receive a detection result of the sensor module, generate hydrogen concentration information corresponding to resistance value information included in the detection result, and remotely transmit information corresponding to the generated hydrogen concentration information, wherein the sensor module further includes a position controller that is configured to change a position of the member, and the computing environment is configured to control an operation of the position controller so that the member is not located in the transformer after receiving a first detection result during a first measurement period of the sensor module, control the operation of the position controller so that at least a portion of the member is located in the transformer, and receive a second detection result during a second measurement period of the sensor module when at least a portion of the member is located in the transformer.

16. The system of claim 15, wherein the member includes carbon nanotubes.

17. The system of claim 15, wherein the member is disposed in an oil drain valve so that insulating oil included in the transformer does not pass through the oil drain valve.

18. The system of claim 15, wherein the computing environment is configured to generate state information of the transformer corresponding to the generated hydrogen concentration information and remotely transmits the generated state information, and the state information includes at least two of a partial discharge, an arc, and an overheating.

19. The system of claim 15, further comprising a human-machine interface (HMI) receiving information corresponding to the hydrogen concentration information from the computing environment, wherein the HMI transmits a control signal to the computing environment, and the computing environment is configured to control an on-off operation of the transformer based on the control signal.

\* \* \* \* \*